United States Patent [19]

Enegren et al.

[11] Patent Number: 4,955,861
[45] Date of Patent: Sep. 11, 1990

[54] DUAL ACCESS INFUSION AND MONITORING SYSTEM

[75] Inventors: Bradley J. Enegren, Norfolk; Gerald S. Melsky, Lexington; Frank R. Prosl, Duxbury, all of Mass.

[73] Assignee: Therex Corp., Walpole, Mass.

[21] Appl. No.: 184,352

[22] Filed: Apr. 21, 1988

[51] Int. Cl.$^5$ .............................................. A61M 1/00
[52] U.S. Cl. .................... 604/141; 604/411; 604/93; 604/175
[58] Field of Search ............... 604/93, 175, 48, 131, 604/140, 141, 891.1, 44, 45, 411, 414; 141/329, 330

[56] References Cited

U.S. PATENT DOCUMENTS

| | | | |
|---|---|---|---|
| 2,911,123 | 11/1959 | Saccomanno | 604/411 |
| 3,552,441 | 1/1971 | Luhleich | |
| 3,730,170 | 5/1973 | Michael | |
| 3,731,681 | 5/1973 | Blackshear et al. | |
| 4,193,397 | 3/1980 | Tucker | |
| 4,258,711 | 3/1981 | Tucker | |
| 4,496,343 | 1/1985 | Prosl | |
| 4,525,165 | 6/1985 | Fischell | |
| 4,571,749 | 2/1986 | Fischell | 600/31 |
| 4,692,146 | 9/1987 | Hilger | 604/93 |
| 4,692,151 | 9/1987 | Blackman | 604/141 |
| 4,695,273 | 9/1987 | Brown | 604/175 |
| 4,710,174 | 12/1987 | Moden et al. | 604/175 |
| 4,737,150 | 4/1988 | Baeumle et al. | 604/411 |
| 4,820,273 | 4/1989 | Reinicke | 604/891.1 |

FOREIGN PATENT DOCUMENTS

| | | |
|---|---|---|
| 0000041 | 1/1978 | European Pat. Off. |
| 0241159 | 10/1987 | European Pat. Off. |
| 075469 | 5/1961 | France ............... 604/411 |
| 2192338 | 1/1988 | United Kingdom |

Primary Examiner—Stephen C. Pellegrino
Assistant Examiner—Kathleen A. Daley
Attorney, Agent, or Firm—Nutter, McClennen & Fish

[57] ABSTRACT

A dual access infusion or monitoring system comprises implantable apparatus and an injection needle. This system enables one to introduce into or withdraw from the apparatus, after it is implanted, a plurality of fluids simultaneously with only a single penetration of the patient's skin. The implantable apparatus includes a sealed housing with an inlet passage extending into the housing which passage has an outer end adjacent to the housing surface and an inner end located inside the housing. A needle stop is positioned at the inner end of that passage and self-sealing septa are mounted at different locations along the passage at selected spacings from the needle stop so as to divide the passage into aligned compartments or segments each of which has its own fluid outlet. The injection needle includes a plurality of lumens, the number of same corresponding to the number of different compartments in the apparatus housing. The proximal ends of the lumens are connected to different passages in a hub and the lumens have outlet openings spaced at different locations along the needle from the needle tip in correspondence with the spacings of the housing passage compartments so that when the needle is inserted into the housing passage through the septa until the needle bottoms on the needle stop, each outlet opening in the needle will be positioned in a different compartment in the housing passage, with all of the needle openings being isolated in a fluid-tight manner from one another and from the atmosphere by at least one septum.

11 Claims, 1 Drawing Sheet

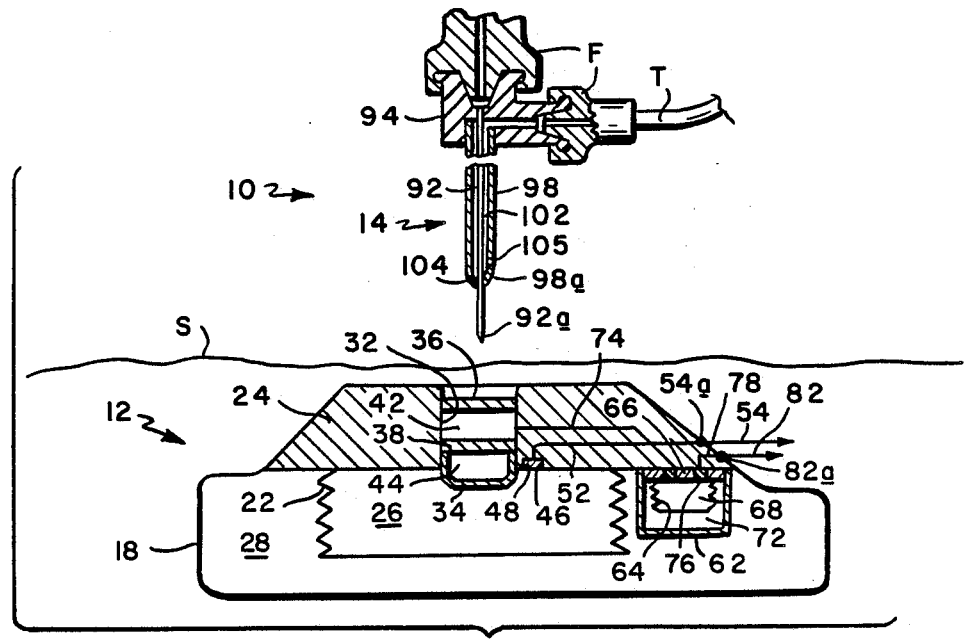
FIG. 1
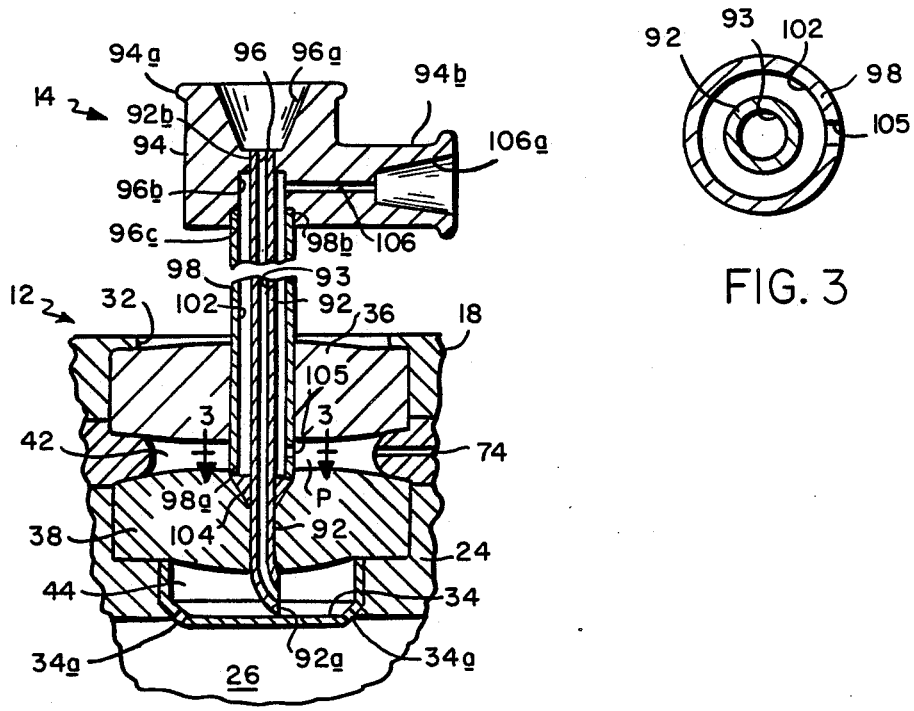
FIG. 2
FIG. 3

DUAL ACCESS INFUSION AND MONITORING SYSTEM

This invention relates to an implantable infusion or monitoring system. It relates more particularly to means for accessing simultaneously from outside the body two or more inlet ports of an implanted infusate pump or portal and thereby two or more infusion or monitoring sites within the body.

BACKGROUND OF THE INVENTION

Over the last ten years or so, drug infusion pumps have been developed which can be implanted in the body and remain there for a relatively long period of time to dispense small measured doses of medication to a selected infusion site in the body. The pump chamber can be refilled with infusate without having to remove the pump from the body by injecting additional infusate transcutaneously through a penetrable septum in the pump wall which septum is located directly under the patient's skin. In some pumps, the refilling of the device also recharges the device's power source. The main advantage of dosing devices of this type is that medication can be routed to the site where it is needed, rather being injected into the bloodstream so that it spreads throughout the body.

Some implantable infusion apparatus have dual pumping chambers enabling them to dispense different infusate concentrations or even different infusates to the same or different infusion sites in the patient's body. The two pumping chambers are purged and refilled independently by way of separate inlet ports at different locations on the pump wall, each port having its own needle-penetrable septum located underneath the patient's skin. An example of this type of pump is disclosed in U.S. Pat. No. 4,258,711.

Another known implantable infusate-dispensing apparatus has, instead of a second pumping chamber, an injection portal incorporated into the pump wall. This portal is basically a chamber with an outlet tube leading to an infusion site in the patient's body and an inlet port closed by a needle-penetrable septum located underneath the patient's skin and which is accessible by transcutaneous injection. This type of device dispenses a continuous flow of infusate to the patient. Then, if a bolus dose or supplemental medication is required, this is administered by percutaneous injection into the portal. Such a device can also be used for blood withdrawal. Apparatus of this type is shown, for example, in U.S. Pat. No. 4,496,343.

In some cases, a patient's drug protocol may call for periodic injection of two different drugs over a long period of time. In this event, such a patient might be fitted with two or more implanted injection portals so that a particular infusate can be supplied to two different sites in the body or so that different drugs can be routed to the same infusion site.

It is apparent from the foregoing that once these implantable pumps and portals have been surgically implanted in the patient's body, the positions of their various inlet ports are more or less fixed with respect to the overlying skin area of the patient. Therefore, each time the physician must inject additional infusate into a particular inlet port in the implanted apparatus, he must penetrate or puncture the skin at substantially the same location. Over a period of time, then, a patient may receive many such needle penetrations in order to service the implanted device.

In this connection, we should mention that when introducing infusate into an implanted pump or portal, the normal procedure is to insert a cannula or needle into that device's inlet port and allow the drug in the reservoir to flow out (i.e. the reservoir is at a higher pressure than the needle or cannula lumen). Then, when the reservoir is empty, a fixed volume of the fresh infusate is injected into the pump or portal through the needle, after which the needle is withdrawn. It is apparent, therefore, that this refilling procedure is a time consuming process that requires the patient to remain still while the needles penetrating his body introduce and/or drain the various fluids from the infusion device implanted in his body. In many instances this procedure is performed in a clinic or physician's office or on a hospital outpatient basis. Therefore, each office visit can be quite time consuming and expensive.

Another disadvantage of the prior techniques for servicing plural port implantable devices of this general type is their propensity for being refilled with the wrong fluid. More particularly, after the device is implanted, its position may change somewhat relative to a fixed spot on the patient's skin surface due to changes in the patient's body weight, for example. Therefore, when refilling or purging the device, it is quite easy for a nurse to insert a needle into the wrong inlet port if she is not very careful. In a dual-chamber infusate pump, for example, this could result in the basal reservoir of the pump being refilled with bolus infusate and the bolus reservoir being charged with lower concentration basal infusate, or it could result in one reservoir of that pump being emptied and filled twice and the other reservoir not being serviced at all.

It would be desirable, therefore, if the number and duration of transcutaneous injections required to access or to service an implanted pump or portal could be minimized, along with the potential for servicing errors. This would not only reduce the risk of infection to the patient, it would also reduce the incidence of epidermal problems associated with implanted access or drug infusion devices of this type, and it would certainly reduce the physical and emotional stress on a patient required to have such an implanted device.

SUMMARY OF THE INVENTION

Accordingly, it is an object of the present invention to provide an improved implantable dual-access infusion or monitoring system.

Another object of the invention is to provide improved means for accessing simultaneously two or more internal infusate chambers of an implantable infusion device.

A further object of the invention is to provide a needle or cannula for accessing simultaneously at least two internal chambers of an implantable infusion apparatus.

Another object is to provide apparatus for enabling individual access from without simultaneously to a plurality of sites inside a patient's body.

Still another object is to provide apparatus of this type which prevents a nurse or physician from accessing the wrong internal chamber of the implanted apparatus when servicing the apparatus.

Yet another object of the invention is to provide apparatus which minimizes the number and duration of skin penetrations or punctures required to properly service a plural-chamber implantable infusion device by transcutaneous injection into the device.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

Briefly, in accordance with this invention, the two or more inlet ports of a plural-chamber infusion pump or access portal are stacked one over the other and are isolated from one another by spaced-apart, needle-penetrable septa so that all of the ports in the implanted device are located at different levels underneath the same spot on the patient's skin.

In addition, injection means are provided which have at least two parallel fluid paths or lumens. The lumens have separate inlets which permit fluid to be introduced into or withdrawn from each needle flow path or lumen independently or to be monitored independently. The injection means lumens also have separate outlets which are located at different elevations on the injection means. Moreover, the spacing along the injection means between the outlets is related to the spacings of the stacked inlet ports in the implanted device so that when the injection means are punctured through the patient's skin into the device through the latter's penetrable septa, the outlet of each lumen will automatically be in fluid communication only with the proper one of the implanted device's inlet ports.

Thus, with a single puncture of a patient's skin, all chambers of a plural-chamber implanted device or portal can be accessed independently at the same time. For example, if the implanted device is a dual chamber infusion pump, the two injection needle inlets can be connected to two different infusate sources so that the two chambers of the implanted device can be filled simultaneously with different drugs. Alternatively, if one needle inlet is connected to an infusate source and the other inlet is connected to a source of negative pressure, one apparatus chamber can be filled with fresh infusate while old infusate is being withdrawn from the other chamber. As still another example, for an implanted device in which one inlet port leads to an infusate chamber and the other inlet port constitutes an injection portal leading to an infusate site in the patient's body, a bolus dose of infusate can be infused into the patient via the injection needle and the portal, while the pump chamber is being flushed out or refilled.

In all of these examples, the combination of the dual channel injection means and the implanted dual chamber infusion apparatus with stacked inlet ports permits two independent operations to be performed simultaneously on the implanted device with a single needle penetration. Although our apparatus allows simultaneous access to all of the internal chambers of the implanted device, one does not, of course, have to perform the flow operations simultaneously. The point is that our apparatus reduces the number of skin punctures necessary to service the implanted apparatus, it also reduces the length of time that the patient has to be inconvenienced by needles or cannulae penetrating his epidermis. This should, in turn, make the wearing of such an implanted device much more bearable to the patient.

It is important to note also that since the injection means or needle fluid paths are "keyed" to the stack of inlet ports in the implanted apparatus by the unique placement of each one of the corresponding needle opening-port pairs, there is no possibility of the injection means accessing the wrong chamber of the apparatus.

The needle-apparatus combination comprising our invention also allows individual access from outside the body simultaneously to a plurality of monitoring sites inside the body for monitoring the same or different variables at those sites, e.g. pressure, temperature, sugar level, etc.

BRIEF DESCRIPTION OF THE DRAWING

For a fuller understanding of the nature and objects of the invention, reference should be had to the following detailed description, taken in connection with the accompanying drawing, in which:

FIG. 1 is a diagrammatic view of a dual-access infusion system embodying the invention; and FIG. 2 is a view in vertical section and on a much larger scale, showing the FIG. 1 apparatus in greater detail.

DESCRIPTION OF THE PREFERRED EMBODIMENT

Referring to FIG. 1 of the drawing, the present system, shown generally at 10, comprises an implantable dual-chamber infusion or pumping apparatus 12 and a dual-channel injection needle or cannula unit 14 for servicing apparatus 12 after the apparatus is implanted. Apparatus 12 includes a generally cylindrical housing 18 which is in the order of two inches in diameter and one-half inch thick and is made of a biocompatible material such as titanium. Positioned within the container is a bellows capsule 22 having an open end mounted to a header 24 constituting the upper wall of housing 18, the opposite end of the capsule being closed. Thus the capsule defines an infusate chamber 26 inside the capsule and a second chamber 28 outside the capsule, but inside housing 18 which contains a known two-phase fluid which vaporizes at physiological temperatures, e.g. 98.6°.

As shown in FIG. 2, formed in the upper wall of the housing and extending down into the header is a passage 32 which communicates with chamber 26 by way of holes 34a in a needle stop 34 at the lower end of the passage. The outer or upper end of passage 32 is closed by a needle-penetrable septum 36. A second septum 38 is positioned midway along the passage thereby dividing it into an upper or outer compartment 42 and a lower or inner compartment 44. Thus, the lower compartment 44 is in fluid communication with chamber 26 by way of the needle stop holes 34a, but it is isolated from the other compartment 42 by the fluid-tight septum 38. The outer compartment 42, on the other hand, is isolated by septa 38 and 36 from compartment 44 and the region outside housing 18, respectively. Referring again to FIG. 1, formed in header 24 is an outlet port 46 from capsule 22 which contains a filter 48. In the illustrated apparatus 12, the port 46 communicates with an outlet conduit or passage 52 in header 24 which leads to the outer surface of the housing where it is connected to one end 54a of a catheter 54. Usually passage 52 includes a fluid restriction to regulate the flow of fluid through the catheter.

The apparatus 12 specifically illustrated herein also has a separate compartment 62 inside housing 18 which contains a second bellows capsule 64 having an open end mounted to a header 66 at the top of compartment 62, with the opposite end of capsule 64 being closed. Thus, capsule 64 defines an infusate chamber 68 inside the capsule and a second chamber 72 outside the capsule, but inside compartment 62 for containing a two-phase fluid similar to that in chamber 28. Fluid communication is established between the compartment 42 located between septa 36 and 38 and chamber 68 inside bellows capsule 64 by a passage 74 in housing header 24. Also, an outlet port 76 in header 66, which port may include a filter similar to filter 48 and a flow restriction communicates with a conduit or passage 78 in header 24, which leads to the outside surface of housing 18 where it connects to one end 82a of a catheter 82.

Thus, in the illustrated apparatus 12, the passage compartment 42 between septa 36 and 38 constitutes an inlet port for bellows capsule 64, while the inner compartment 44 below septum 38 constitutes an inlet port for bellows capsule 22.

In use, apparatus 12 is implanted in the patient's body, e.g. in a subcutaneous pocket in the patient's abdominal wall and it is positioned so that its septum 36 is located directly underneath the patient's skin S. Catheters 54 and 82 may lead to the same infusion site in the patient or to different sites depending upon the particular patient's physical problems. Bellows chambers 26 and 68 may be filled with the same infusates in different concentrations or with different drugs. Chambers 28 and 72 are filled with two-phase fluids which vaporize at physiological temperatures so that they exert a pressure on bellows capsules 22 and 64, respectively, tending to collapse them. These forces tend to expell the infusates from the capsules through their respective outlet passages 52 and 78 to catheters 54 and 82 respectively. The operation of such pumps with fluid power cells is well known from U.S. Pat. No. 3,731,681, as well as from the patents identified above. Also, although catheters 54 and 82 are shown separately in the drawing, they could just as well be the two lumens of a double lumen catheter of the type sold, for example, by HDC Corporation, Mountain View, California (Stock No. 330-12).

When the supply of infusate in chamber 26 is exhausted, the chamber can be refilled by injecting fresh infusate transcutaneously into passage compartment 44 using needle or cannula unit 14. The extension of the bellows capsule 22 that occurs during the refilling operation exerts a pressure on the two-phase fluid in chamber 28 causing that fluid to condense thereby recharging the fluid power cell that collapses capsule 22 as described in the above patents.

In like manner, when the bellows capsule 64 is empty of infusate, it can be refilled and its power cell recharged using needle unit 14 by injecting fresh infusate into passage compartment 42 which constitutes the inlet port for the bellows chamber 68.

The implantable apparatus 12 specifically depicted herein is a dual-chamber pump with two outlet catheters which enables the apparatus to independently pump the same infusate to different infusion sites in the patient's body or different infusates to the same infusion site, with the bellows capsules 22 and 64 being emptied and refilled independently of one another. Apparatus 12 may also be of the type described in the above-mentioned U.S. Pat. No. 4,258,711 which has only a single outlet catheter that delivers the infusates from both pump chambers 26 and 68 to the same infusion site. In this event, the outlet passage 78 from chamber 68 would join outlet passage 74 from chamber 26 at a Y-connection so that fluids flowing along both of those paths would be routed to the single catheter 54. Alternatively, the outlets from the two chambers may be routed to a double lumen catheter of the type described above.

Still another apparatus embodiment may be arranged to dispense basal and bolus infusate doses in the manner of the device described in the aforementioned U.S. Pat. No. 4,496,343. That apparatus pumps a basal dose of infusate in a controlled manner to the patient, with such basal dose being supplemented from time to time by a bolus dose injected directly into a portal leading to the infusion site. To modify apparatus 12 to operate in this fashion, compartment 62, capsule 64 and the outlet catheter 82 would be eliminated and passage 74 leading from passage compartment 42 would be connected by a Y-connection to passage 52 so that a bolus infusate dose injected into compartment 42 would be conducted directly to the infusion site. As described in that patent, passage 74 should include a check valve (not shown) to prevent reverse flow of infusate from compartment 42 back into bellows capsule 22 during a bolus injection.

Also, of course, the implanted apparatus 12 may consist simply of a stack of independent injection portals similar to compartments 42 and 44, each portal being isolated from its neighbors by a septum similar to septum 36 and having its own outlet passage leading exteriorly of the housing for connection to a catheter. In this way, individual portals may be dedicated to carry to a particular infusate to a selected infusion site in the patient's body, access to each portal being had by transcutaneous injection into that portal of the portal stack.

As a further application, the portal unit may be used to provide access for pressure monitoring at different points in the body. In this event, the catheters leading from each portal of the unit would extend to a different arterial or venous monitoring site and be filled with fluid. The plural lumen needle inserted into the portal unit would be connected by tubing, also filled with fluid, to different channels of a pressure recorder or monitor.

Referring now particularly to FIGS. 2 and 3 of the drawing, after apparatus 12, in one of its aforesaid versions, is implanted under the skin S as shown, its infusate chambers 26 and 68 are accessed by inserting the needle or cannula unit 14 through septa 36 and 38 into passage 32 until it bottoms on the needle stop 34 at the inner end of passage 32. Unit 14 comprises a more or less conventional hypodermic needle 92 having a tip 92a which is preferably of the Huber-type and a lumen 93 extending the length of the needle.

The upper end 92b of needle 92 is joined to a metal or plastic hub 94 where the needle lumen 93 communicates with a collinear passage 96 in the hub. The hub upper end 94a and a flared upper end 96a of passage 96 are configured as a female Luer-type connector so that as shown in FIG. 1, the hub end 94a can be releasably coupled to a mating fitting F on a tube T leading from a standard infusate source such as a syringe or to a source of negative pressure.

Surrounding needle 92 partway along its length is a length of hypodermic tubing 98 whose inner diameter is slightly larger than the outer diameter of needle 92 thereby leaving an annular channel or gap 102 between the needle and the tube. The lower end 98a of tubing 98 is connected to the outside wall of needle 92 by an annular weld or brazing fillet 104 so that there is a fluid-tight seal at that location. Also, a small hole 105 is present in the wall of tubing 98 just above fillet 104.

The hub passage 96 has a relatively deep counterbore 96b extending in from the underside of the hub and a larger diameter, shallower counterbore 96c. The upper end 98b of tube 98 is secured in counterbore 98c by a suitable epoxy cement, with counterbore 96b being essentially an extension of gap 102. Hub 94 is provided also with a lateral extension 94b which contains a lateral passage 106. The passage inner end intercepts counterbore 96b above tubing 98, while the flared passage outer end 106a and extension 94b are shaped to form a female Luer-type connector. This allows hub section 94b to be coupled to a mating Luer-lock fitting F at the end of a tube T leading to a second infusate source or to a negative pressure source as seen in FIG. 1.

Referring to FIG. 2, in accordance with the invention, the spacing of the tubing hole 105 above the needle tip 92a where the lower end of the needle lumen 93 is located corresponds to the spacing between the needle stop 34 in apparatus 12 and a point P midway along the passage compartment 42 therein. Resultantly, when needle unit 14 is inserted into passage 32 so that its needle tip 92a engages or bottoms on needle stop 34, the lower end of the needle lumen 93 will automatically be located in passage compartment 44, while the tubing hole 105 will be located in passage compartment 42. Therefore, due to the presence of septa 36 and 38 in that passage, and the above described fluid paths in apparatus 12, the needle lumen 93 will be in fluid communication only with bellows chamber 26, whereas tubing passage 102 will be in fluid communication only with infusate chamber 68. Resultantly, if hub sections 94a and 94b are both connected to sources of negative pressure, the liquids in bellows chambers 26 and 68 can be withdrawn independently from those chambers at the same time. By the same token, if the hub sections are coupled to different infusate sources, the two pump chambers in apparatus 12 can be recharged and refilled with different infusates simultaneously. Still further, if one of the passage compartments, say compartment 42, constitutes an injection portal communicating directly with the catheter 54, the hub section 96b can be connected to a syringe so that while the pump chamber 26 is being emptied or refilled with infusate via hub section 94a, needle 92 and passage compartment 44, a bolus dose of infusate can be administered to the patient via hub section 94b, passage 102 and passage compartment 42.

It is apparent from the foregoing, then, that using an implantable apparatus with stacked inlet ports, such as apparatus 12, and a plural channel needle unit such as unit 14, different fluids may be introduced into or withdrawn from the various chambers of the apparatus 12 independently and simultaneously after only a single puncture of the patient's skin to insert unit 14 into passage 32 of the implanted apparatus. The invention thus allows individual access simultaneously to a plurality of sites in a patient's body for purposes of introducing fluids into or withdrawing them from the body, or for measuring or monitoring pressure or other functions or variables at those sites. Moreover, the invention provides access in such a way as to prevent establishment of fluid communication between any flow path in the needle or cannula and the incorrect inlet port of the implanted device.

While there is shown infusion apparatus having a dual chamber capability and a needle unit 14 with two fluid channels, it is obvious that the principles disclosed here can be extended to implantable apparatus with a stack of three or more inlet ports or compartments which can be accessed simultaneously in a single penetration of the patient by a needle unit having a corresponding number of flow channels whose outlets are spaced from the unit's tip to correspond to the positions of the ports in the stack. Also, of course, the implanted apparatus may be accessed by separate needles or cannulae each one having its lumen outlet positioned along the needle to align with only one of the apparatus inlet ports or passages when the needle is inserted into the implanted apparatus.

It will thus be seen that the objects set forth above, among those made apparent from the preceding description, are efficiently attained and, since certain changes may be made in the above construction without departing from the scope of the invention, it is intended that all matter contained in the above description or shown in the accompanying drawing be interpreted as illustrative and not in a limiting sense.

What is claimed as new and desired to be secured by Letters Patent of the United States is:

1. A dual access infusion or monitoring system comprising in combination
   A. implantable apparatus having
      1. a biocompatible hermetically sealed housing,
      2. an inlet passage extending into said housing from an exterior surface thereof, said passage having an outer end adjacent to said housing surface and an inner end located inside the housing,
      3. needle stop means at the inner end of said passage;
      4. a plurality of needle-penetrable, self-sealing septa mounted in said passage at selected different spacings from said needle stop thereby to divide said passage into a plurality of aligned segments; and
      5. means defining separate fluid outlets from said passage segments,
      6. an infusate pump inside the housing in fluid communication with one of said housing passage segment fluid outlets,
      7. a catheter extending out of said housing, said catheter having at least one lumen for conducting fluid from said pump to an infusion site, and
      8. a first fluid outlet in the housing for conducting fluid from said pump to said catheter, and
   B. fluid injection means including
      1. a plurality of tubes having proximal and distal ends and separate axial lumens therebetween, the number of tubes in the injection means corresponding to the number of passage segments in the implantable apparatus housing,
      2. hub means mounted to the proximal ends of said tubes,
      3. means defining separate fluid passages in said hub means extending from different surface locations on the hub means to the lumens of different ones of said tubes, and
      4. means in said tubes defining outlets from said tube lumens, the axial spacings of said outlets along said injection means corresponding substantially to the spacings of said housing passage segments in said implantable apparatus so that when the injection means are inserted through said septa into said housing passage until the injection means bottom on said needle stop means, said tube outlets are positioned in different ones of said passage segments so that they are isolated from one another and from the atmosphere by at least one septum whereby separate fluid-tight fluid paths exist between said hub means surface locations and said housing passage segment outlets.

2. The system defined in claim 1 and further including a second outlet conduit in said housing for conducting fluid from another one of said housing passage segment outlets to said catheter so that while the pump is being filled with or emptied of fluid via one of said injection means tubes, a fluid can be flowed directly to an infusion site via another one of said injection means tubes.

3. The system defined in claim 2 wherein
   A. the catheter is a dual lumen catheter; and
   B. said first and second outlet conduits are in fluid communication with different lumens of said catheter.

4. The system defined in claim 1 wherein said implantable apparatus also includes
   A. a second infusate pump inside the housing;
   B. a second outlet conduit for conducting fluid from another one of said housing passage segment outlets to said second pump; and
   C. a third outlet conduit in said housing for conducting fluid from said second pump to said catheter.

5. The system defined in claim 1 wherein at least two of said housing passage segment fluid outlets lead to different locations on said housing exterior surface.

6. The system defined in claim 1 wherein
   A. the injection means comprise a pair of concentric inner and outer tubes;
   B. a fluid tight seal extends between the distal end of the outer tube and the outside surface of the inner tube; and
   C. the outlets in said inner and outer tubes are located adjacent to the distal ends of those tubes.

7. The system defined in claim 6 wherein the distal end of said inner tube is formed with a Huber-type tip.

8. The system defined in claim 1 and further including fluid coupling means on the injection means hub exterior for releasably connecting said hub passages in a fluid-tight manner to different fluid paths exterior to said injection means.

9. A dual access infusion or monitoring system comprising injection needle means having a longitudinal axis and a tip, said means including
   A. concentric inner and outer tubes permanently fixed to one another, said inner tube being longer than said outer tube and each tube having proximal and distal ends and an unobstructed axial lumen therebetween;
   B. a hub mounted to the proximal end of said tubes;
   C. first and second fluid passages in said hub extending from different surface locations on the hub exterior surface to different ones of said tube lumens;
   D. a fluid-tight seal extending from the distal end of said outer tube and the outside wall of said inner tube, and
   E. means defining openings in said tubes that provide outlets from the corresponding lumens of those tubes, said openings being located at selected fixed different axial spacings from said needle means tip so that fluids introduced into said first and second passages can flow simultaneously along said needle means and exit therefrom at said selected different spacings from said tip.

10. The system defined in claim 9 wherein the distal end of said inner cannula is formed with a Huber-type tip.

11. The system defined in claim 9 and further including fluid coupling means on the hub exterior for releasably connecting said hub passages in a fluid-tight manner to different fluid paths exterior to said needle means.

* * * * *